United States Patent [19]

Kaufman

[11] Patent Number: 4,882,150

[45] Date of Patent: Nov. 21, 1989

[54] DRUG DELIVERY SYSTEM

[76] Inventor: Herbert E. Kaufman, 300 Lake Marina Dr., Unit 18E, New Orleans, La. 70124

[21] Appl. No.: 345,170

[22] Filed: May 1, 1989

Related U.S. Application Data

[62] Division of Ser. No. 202,184, Jun. 3, 1988.

[51] Int. Cl.$^4$ ............................................. A61K 9/22
[52] U.S. Cl. ..................................... 424/428; 424/427
[58] Field of Search ................. 424/428, 427; 514/912

[56] References Cited

U.S. PATENT DOCUMENTS

| | | |
|---|---|---|
| 3,826,258 | 7/1974 | Abraham . |
| 3,845,201 | 10/1974 | Haddad et al. . |
| 3,914,402 | 10/1975 | Shell . |
| 4,001,388 | 1/1977 | Shell . |
| 4,115,544 | 9/1978 | Shell . |
| 4,164,559 | 8/1979 | Mujata et al. . |
| 4,179,497 | 12/1979 | Cohen et al. . |
| 4,432,964 | 2/1984 | Shell et al. . |

OTHER PUBLICATIONS

"Collagen as a Vehicle for Drug Delivery", Rubin et al., Journal of Clinical Pharmacology, Aug.-Sep. 1973.
"Collagen as a Biomaterial", Stengel et al., pp. 231–253, ©1974.
"Principles of Polymer Chemistry", Flory, pp. 49–68.
"Flow of Gases Through Polyethylene", Michaels et al., Journal of Polymer Science, vol. 1, pp. 413–439, 1961.
"Contact Tins Practice", Manall, pp. 159–165, 1965.
"Chemistry and Industry", Jul. 1970, p. 905.

Primary Examiner—Joseph L. Schofer
Assistant Examiner—Thomas McDonald, Jr.
Attorney, Agent, or Firm—Barnes & Thornburg

[57] ABSTRACT

An ophthalmic drug delivery system is provided which includes at least one particle of bioerodible material, and a liquid or ointment carrier which includes ophthalmic drug to be delivered to the ocular area. A process of making the system and a method of treatment are also provided.

10 Claims, 1 Drawing Sheet

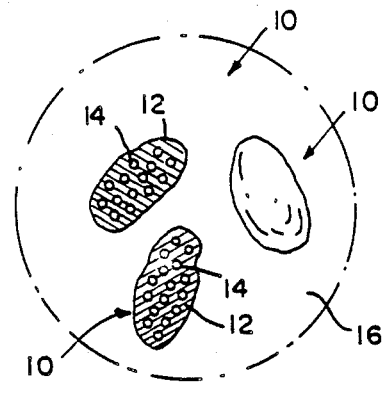
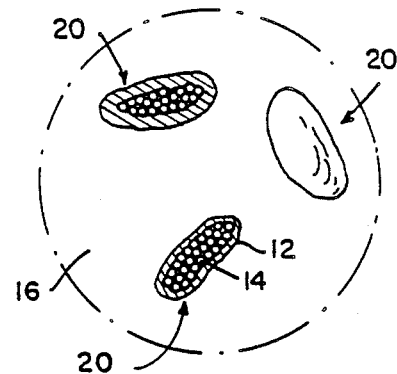
FIG. 1     FIG. 2
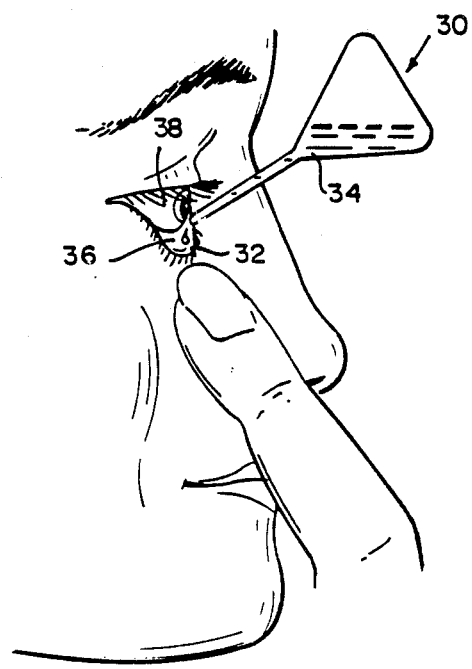
FIG. 3

DRUG DELIVERY SYSTEM

This is a divisional of application Ser. No. 07/202,184, filed June 3, 1988.

BACKGROUND AND SUMMARY OF THE INVENTION

The invention relates to a drug delivery treatment system and method of making the system and method of treating the eye.

Most ocular treatments require frequent topical administration of drugs to the tissues of the ocular cavity.

When medication must be applied topically to the eye, one common form of treatment is the use of liquid drops. The liquid drop form is extremely easy to use as the patient merely self-administers the liquid through an eye dropper or dispenser which includes an eye drop extension end. However, a substantial disadvantage of the liquid form is that the medication or lubricating solution rapidly drains from the ocular cavity into the nasal cavity through an opening called the punctum. Further, the liquid may simply evaporate from the eye.

Thus, with the use of liquid treatments, a continuous prolonged delivery of medication is not achieved, and the exact dosage is unpredictable as liquid drains out of the eye. Even with intermittent administration, the liquid treatment will continue to rapidly wash out of the eye, and the continued problem of unpredictability of dosage remains. Further, continuous administration of liquid is not only inconvenient, but may be dangerous.

Several systems shown in U.S. patents provide large ocular inserts to deliver drug to an eye continuously. Certain inserts disperse the drug and require removal of the carrier of the drug once the drug has been delivered. However, U.S. Pat. Nos. 3,845,201; 4,164,559 and 4,179,497 show various inserts in the form of large pellets which dispense drug over a period of time and eventually are completely eroded, and thus do not require removal after drug delivery.

These inserts have certain advantages over the liquid treatments as more predictable dosage is obtained as there is a continuous dispensing of the drug over a period of time without rapid washout. Thus, the unitary ocular inserts provide predictable dosage over a period of time without the requirement of repeated applications as required with liquid treatments.

However, there are certain disadvantages which accompany the use of large unitary ocular inserts. These unitary inserts must be carefully placed under the eyelid, and require special care and special insert devices for insertion. Difficulties in patient education for inserting these in compliance with proper technique have prevented their widespread use.

In an attempt to address the problems of liquid treatments and ocular inserts, U.S. Pat. Nos. 3,914,402; 4,001,388 and 4,115,554 all to Shell, show ophthalmic forms which include a suspension of solid particles from 10 to 300 microns in largest dimension in a liquid medium. The liquid medium in the Shell patents is used exclusively as a carrier for suspending the particles and delivering the particles to the eye. The Shell dosage form alleviates certain problems associated with ocular inserts, including the complication of insertion and requirement for special insertion devices. However, the liquid carrier in Shell does not include drug therein, and therefore, the liquid does not deliver drug to the ocular environment. Only the minute particles can be relied on for drug delivery. Treatment with the Shell patent system depends on the chance of the particles becoming lodged in the eye tissue, as the liquid delivers no drug. Further, as no drug is included in the liquid, all the medication which is limited to inclusion in the particles, could feasibly wash out of the eye with the particles through the punctum which is about 0.5 mm in diameter. Thus, Shell may effectively deliver no drug at all to the ocular environment, as the particles may drain out of the eye prior to release of the medication from the particles.

Although Shell asserts that the particles do not drain from the ocular cavity through the punctum, in practice if the particles are substantially smaller in diameter than the punctum, these particles will wash and drain out of the eye in the normal course of drainage of the suspension liquid through the natural duct system of the ocular cavity. As the Particles in Shell are delivered in a liquid suspension, the excess liquid delivered to the eye would naturally drain through the punctum. Further, liquid contact alone with the eye would provide no medication to the ocular environment as the liquid is free of medication.

U.S. Pat No. 3,826,258 to Abraham shows a gradual release medicine carrier. Abraham addresses topical treatment of the eye using capsules which are dropped into the eye. Similar to the Shell system, the liquid carrier in the Abraham patent is used merely to suspend the capsules and deliver the capsules to the eye. Abraham neither shows nor suggests including drug in the liquid carrier solution.

Thus, an object of the present invention is to provide a drug delivery system, a method of making the drug delivery system and a method of treatment which includes the advantages of drug solution treatments, insert treatments and suspension treatments.

It is a further object to provide a treatment system method which delivers a dependable dosage or amount of treatment media to the eye. It is a further object to provide an ophthalmic treatment system easily administered to the eye which will remain in the ocular cavity over a period of time.

It is yet another object to provide a system which provides prolonged drug delivery as well as instant delivery of drug to the eye.

These and other objects are achieved by providing an ophthalmic drug delivery system which includes at least one particle of bioerodible material. The particle or particles are suspended in one of a liquid carrier and an ointment carrier containing ophthalmic drug and having a pH acceptable to the eye.

The drug delivery system provides prolonged delivery of drug to the eye as drug in the solution is absorbed into the particles of bioerodible material prior to administration and/or after administration to the eye. The drug absorbed in the bioerodible material will be released over a period of time as the particles erode in the ocular environment. Further, an instant delivery of drug to the eye is provided by the drug in the liquid or ointment carrier. Thus, where instant delivery is needed, the liquid carrier provides instant release of drug and the particles provide prolonged release of drug.

According to other advantages of certain preferred embodiments of the invention, the particles can include drug dispersed therein prior to suspension into the carrier solution. Thus, in certain preferred embodiments a different drug can be provided in the particles for prolonged administration than the drug contained in the liquid medium. Further, according to certain preferred embodiments, the concentration of drug in the particles is such that when placed in a carrier solution having a different drug, the equilibrium between the two will be such that drug in the carrier solution will absorb into the particles. Thus, the particles will include different types of drug disposed therein for prolonged delivery.

According to other advantageous features of certain preferred embodiments of the invention, the specific equilibrium between drug in the particle and drug in the carrier liquid provides a specific amount of drug in the particle to be delivered over a specific duration when administered to the ocular area.

Methods for making the drug delivery system and methods of treating the eye using the drug delivery system are also provided.

Other objects, advantages and novel features of the present invention will become apparent from the following detailed description of the invention when considered in conjunction with the accompanying drawings.

BRIEF DESCRIPTION OF THE DRAWINGS

FIG. 1 is a magnified view of the particles of bioerodible material according to certain embodiments of the present invention;

FIG. 2 is a magnified view of particles of the bioerodible material according to other advantageous embodiments of the present invention; and FIG. 3 is a pictorial view showing administration of the ophthalmic treatment system into the conjunctival sac of the eye.

DETAILED DESCRIPTION OF THE DRAWINGS

In its simplest form, the present eye treatment system includes particles of bioerodible material, which are suspended in a liquid carrier or ointment carrier having at least one drug therein and having a pH acceptable to the eye. The liquid medium employed in the present suspension system may be an aqueous or non-aqueous ophthalmically acceptable sterile liquid. Suitable non-aqueous liquid media include the physiologically acceptable oils such as silicon oil, USP mineral oil, white oil, and vegetable oils, for example, corn oil, peanut oil or the like.

To achieve a uniform dispersion of the particles in the liquid, the density of the liquid medium can be chosen such that it is equal to the density of the particles Therefore, the particles will not float to the top of the liquid or sink to the bottom. If the liquid medium does not have the same density of the particles, the viscosity of the liquid medium can be adjusted in order to provide a uniform dispersion, or the dispensing system can achieve a dispension by shaking or proper mixing immediately before administration.

In certain embodiments, the eye treatment liquid medium contains a variety of other materials to adjust pH, render the medium isotonic, preserve the treatment system and the like. Preservative agents which can be used include benzalkonium chloride in a concentration range of from 1:15,000 to 1:30,000; chlorobutanol in a concentration range of from 0.3% to 0.8%; thimerosol in a concentration range of from 0.001% to 0.003%; and phenyl mercuric nitrate in a concentration range of from 1:60,000 to 1:80,000. Also, in certain preferred embodiments, unpreserved unit or daily dose systems can be used. Other agents may be added to increase viscosity, promote suspension and/or improve ocular compatibility, such as methyl cellulose in an amount of from 0 1% to 0.7% or poly (vinyl alcohol) in an amount of from 0.4% to 2.0%. These and other additive materials are known in the art. A variety of these materials is generally described in the book *Contact Lens Practice,* Robert B. Mandell (Charles C. Thomas, 1965) at pp. 159–165, which description is herein incorporated by reference.

In certain preferred embodiments, instead of using a liquid medium for the suspension, the particles can be suspended in an ointment such as lanolin, petrolatum and other known ointments.

Medication or drugs are included directly in the liquid or ointment carrier. The term "drug" is used in this description in its broadest sense, and covers all drugs used in any mammal. Drugs which are useful in the ocular area are specifically desired, although the present invention is not limited to only ocular drugs. The term "drug" is defined in the present invention as including, but not limited to the following classes of drugs: therapeutic drugs, preventative drugs, diagnostic drugs and any other drugs. It is to be understood that a variety of classes, subclasses and specific examples of drugs not expressly mentioned herein are within the scope of this invention and other examples of drugs are well known and are easily ascertainable to those skilled in the art.

Drugs suitable for incorporation in the particles of the suspension, consistent with their known dosages and uses, are without limitation ophthalmic drugs including: antibiotics such as tetracycline, chlortetracyline, bacitracin, neomycin, polymyxin, gramicidin, oxytetracycline, chloramphenicol, gentamycin, penicillin, kanamycin, amikacin, sisomicin, tobramycin, garamycin, ciprofloxacin, norfloxacin and erythromycin; antibacterials such as sulfonamides, sulfacetamide, sulfamethizole and sulfisoxazole; antivirals, including idoxuridine; and other antibacterial agents such as nitrofurazone and sodium propionate; anti-allergenics such as antazoline, methapyriline, chlorpheniramine, pyrilamin and prophenpyridamine; anti-inflammatories such as cortisone, hydrocortisone, hydrocortisone acetate, dexamethasone, dexamethasone 21-phosphate, fluocinolone, medrysone, prednisolone, methylprednisolone, prednisolone 21-phosphate, prednisolone acetate, fluorometholone, betamethasone, fluocortolone, indomethacin and triamcinolone; decongestants such as phenylephrine, naphazoline and tetrahydrazoline; miotics and anticholinesterases such as pilocarpine, eserine salicylate, carbachol, di-isopropyl fluorophosphate, phospholine iodide, echothiophate, physostigmine and demecarium bromide; mydriatics such as atropine sulfate, cyclopentolate, homotropine, scopolamine, tropicamide, eucatropine, and hydroxyamphetamine; sympathomimetics such as epinephrine and immunosuppressants such as cyclosporin and azathioprine.

According to certain preferred embodiments, drug is included in the particles prior to suspension in the carrier. The drug in the particles can include the same drug as the drug in the carrier and/or different drugs. As will be discussed below, the drug can be dispersed throughout the particles or encapsulated within the particles.

The particles suspended in the liquid or ointment medium should be made of material which is bioerodible such that removal of the particles from the eye is not required as they are broken down and absorbed in the ocular environment (or resorbed). The term "bioerodible" is defined as a material which innocuously disintegrates or breaks down from a unit structure or enclosure over a prolonged period of time in response to the environment of the eye by one or more physiCal or chemical degradative processes, for example, enzymatic action, hydrolysis, ion exchange, dissolution by solubilization, emulsion formation or micelle formation. The bioerosion of the particles not only prevents a build-up of particles in the tissues of the ocular cavity, but also provides prolonged release of the treatment in the eye which can be controlled such that the treatment is predictable.

Bioerodible materials used in the particles of the present suspension of this invention should be non-toxic and compatible with any drug which may be delivered therewith. In certain preferred embodiments, the bioerodible materials should be capable of absorbing drugs in which they are soaked, and in certain other preferred embodiments, the bioerodible materials should be capable of forming films which wholly surround and enclose a drug or other active agent to be delivered to the eye.

The particles should be comfortable when they are under the eyelids, as well as when they are on the surface of the eye in between the eyelids in the interpalpebral area, for example. In certain preferred embodiments, the particles are soft to help assure this comfort.

There are several naturally occurring materials, as well as synthetic materials, which are biodegradable and suitable for the present invention.

Examples of synthetic polymers that can be prepared which are biodegradable include polylactides and polyglycolic acid. These biodegradable polymers are broken down into innocuous products such at carbon dioxide and water and they are also commercially available.

Useful polylactides includes both homopolymers and copolymers. Usually, these polylactides are prepared from the cyclic esters of lactic acids. Both L(+) and D(−) forms of lactic acid may be used to prepare the polylactides as well as the optically inactive DL-lactic acid mixture or any desired mixtures of D(−) and L(+) lactic acids.

Lactide copolymers offer an important degree of flexibility in choosing the life of a polymer matrix since this can be controlled through the amount and type of comonomer used. Some illustrative examples of suitable comonomers include: glycolinde, $\beta$-propiolactone, tetramethylglycolide, $\beta$-butyrolactone, gamma-butyrolactone, pivalolactone, and intermolecular cyclic esters of $\alpha$-hydroxybutyric acid, $\alpha$-hydroxyisobutyic acid, $\alpha$-hydroxyvaleric acid, $\alpha$-hydroxyisovaleric acid, $\alpha$-hydroxycaproic acid, $\alpha$-hydroxy- -ethylbutyric acid, $\alpha$-hydroxyisocaproic acid, $\alpha$-hydroxy $\beta$-methylvaleric acid, $\alpha$-hydroxyheptanoic acid, $\alpha$-hydroxyoctanoic acid, $\alpha$-hydroxydecanoic acid, $\alpha$-hydroxymyristic acid, $\alpha$-hydroxystearic acid, $\alpha$-hydroxylignocenic acid, and $\beta$-phenyllactic acid.

Methods of preparing polylactides are well documented in the patent literature. The following U.S. Patents, the teachings of which are hereby incorporated by reference, describe in detail suitable polylactides, their properties and their preparation: Dorough, 1,995,970; Schneider, 2,703,316; Salzberg, 2,758,987; Zeile, 2,951,828; Higgins, 2,676,945 and 2,683,136; Trehu, 3,531,561; British Patent Specification Nos. 755,447; 799,291; 825,335; 901,037; 932,382; 1,048,088; 1,123,445; West German Patent Nos. 946,664; 975,191; 1,112,293; 1,152,258; 1,153,902; East German Patent No.14,548; French Patent Nos. 1,425,333; 1,478,694; 1,512,182; Netherlands Patent No. 99,836; Netherlands Patent Application Nos. 6,605,197; 6,605,292; Japanese Numbers 17,675 (1966); 7,796 (1967); 2,948 (1968); 15,789 (1969).

Polyglycolic acids have recently been found to possess excellent biodegradable properties. Polyglycolic acid is the homopolymer of glycolic acid (hydroxyacetic acid). In the conversion of glycolic acid to polyglycolic acid, glycolic acid is initially reacted with itself to form the cyclic ester glycolide, which in the presence of heat and a catalyst is converted to a high molecular weight linear-chain polymer. Polyglycolic acids and their properties are described in more detail in the following article, the teachings of which are hereby incorporated by reference: "Cyanamid Research Develops World's First Synthetic Absorbable Suture", *Chemistry and Industry,* July 11, 1970, page 905.

The molecular weights of polypeptides and polyglycolic acid are closely related to both the exudation of the drug and the biodegradation of the matrix. It has been found that high molecular weights, i.e., $Mw=90,000$ or higher result in polymer matrices which retain their structural integrity for longer periods of time, while lower molecular weights, i.e., $Mw=30,000$ or below, result in both slower exudation and shorter matrix lives.

A preferred particle material is collagen such as that obtained from pig sclera or Cow skin and cross-linked with ultraviolet, or other forms of collagen cross-linked either by ultraviolet or X-ray.

The chemistry of a molecular structure and biochemical properties of collagen have been well established. The use of collagen as a vehicle for drug delivery as a bio-material is well known. U.S. Pat No. 1,464,559 to Miyata et al. lists several publications discussing the use of collagen in drug delivery. An example is "Annual Review of Biophysics and Bioengineering", Vol. 3, pp. 231-253, 1974, by Miyata et al. Another example is Rubin et al., *J. Clin. Pharmacol.* Vol. 13 (8/9):309–312 (1973), "Collagen as a Vehicle for Drug Delivery".

Collagen is a major protein of connective tissue such as cornea, skin, etc., and can be solubilized and purified by the treatment with proteolytic enzymes (other than collagenase) such as pepsin. Solubilized collagen is telopeptides-poor, relatively inexpensive, not antigenic and useful as a biomedical material. Enzyme solubilized native collagen is soluble in acidic pH, and soluble at physiological pH and at body temperature.

Native collagen is insoluble at physiological pH and at body temperature. Thus, native collagen must be changed such that the collagen erodes in the ocular environment so that physical removal thereof is not required.

The U.S. Patent to Miyata et al. shows various forms of chemically modified collagen which is erodible in the eye under physiological pH and under normal body temperatures.

Another material which can be used for the particles of the present invention is gelatin which is obtained by the selective hydrolysis of collagen and includes a complex mixture of high molecular weight water soluble proteins.

As used herein, the term cross-linked gelatin means the reaction product of gelatin or a gelatin derivative with a cross-linking agent which is reactive with either the hydroxyl, carboxyl or amino functional groups of the gelatin molecule but is substantially unreactive with the peptide linkages of the gelatin molecule. The product of cross-linking reaction preferably has an average molecular weight of from 20 to 50,000 between cross-links, while higher values can also be employed. These reaction products bioerode in the environment of the eye over a prolonged period of time.

Cross-linked gelatin materials and their preparations are well known. The degree of gelatin cross-linking is dependent upon the processing conditions employed and markedly affects the gelatin's bioerodability. Exemplary cross-linking agents are: aldehydes, such as monoaldehydes, e.g., $C_1$-$C_4$ aldehydes, dialdehydes, epoxides, para-benzene quinone, and aqueous peroxydisulfate.

Aldehydes and ketones, especially the 1 to 4 carbon aldehydes and ketones are preferred, with formaldehyde being a most preferred cross-linking agent.

Irradiation is another suitable method for cross-linking gelatin; see for example Y. Tomoda and M. Tsuda, *J. Poly Sci.*, 54,321 (1961).

The reactive hydroxyl, carboxyl and amino groups are respectively present in gelatin in the appropriate amounts of 100, 75 and 50 meq per 100 grams. These quantities may serve as a general guide in determining the amount of cross-linking agent to be used.

Cross-linked gelatin is relatively permeable to ocular fluid so that diffusion of drug through gelatin may take place to some extent. Thus, cross-linked gelatin is a good example of a release rate-controlling material which releases drug by a diffusion mechanism.

Other materials which can be used for the particles include polymers of polyvinyl alcohol, methyl cellulose, carboxy methyl cellulose, hydroxypropy methylcellulose and lipids, which may include licithin, cholesterol, fatty alcohols and other related materials. Particles can also include methyl cellulose derivatives and can include a combination of the bioerodible materials discussed above. Further, treatment system can include a variety of different types of particles having different components to thereby vary the rate of erosion. Further, certain bioerodible materials may be more advantageous for absorbing and releasing certain active agents to be delivered to the eye.

Crystallinity also affects the exudation and biodegradability rates. The polymer matrices having higher degrees of crystallinity have slower exudation rates and slower biodegradability. It is known that the crystallinity has a marked effect on physical properties. See Flory, Paul J., *Principles of Polymer Chemistry*, 5th printing, 1966 at pp. 49 et seq. It has also been reported in the literature that gaseous diffusion through polymeric membranes is slower, in general, for those polymers having higher degrees of crystallinity. See Michaels, A. S. and Bixler, H. J., "Flow of Gases through Polyethylene and Rubbery Polymers," *J. Poly. Sci.*, vol. 50, pp 413–439 (1961).

A good amount of control over the release of drug can be obtained by choosing appropriate molecular weights and degrees of crystallinity in the polymer matrix. For example, if a relatively long release duration is desired, a high molecular weight polymer formed from a pure optical isomer of lactic acid can be used for the matrix; on the other hand, if a rapid release rate is desirable over a short duration, a low molecular weight lactide copolymer having a lower degree of crystallinity can be synthesized for use as the polymer matrix. Those skilled in the art will know or be able to determine by routine experimentation many suitable combinations of molecular weights and degrees of crystallinities of polylactides or polyglycolic acid to accomplish a desired release rate and duration.

Using one or more of the above parameters, polymeric matrices can be designed which have a great variety of exudation rates and biodegradability. Matrices can be synthesized to have lives shorter than, equal to or longer than the period of effective drug delivery. For the shorter matrix lives, drug delivery will be accomplished by a combination of drug exudation and matrix biodegradation; for the longer matrix lives, drug delivery will be substantially dependent on only drug exudation. The degree of flexibility thus offered in designing drug dispensing system of this invention is of great significance.

Further, the particles of the present invention, according to certain preferred embodiments, should be soft and malleable such that pressure created by the eyelid and the eye will deform the particles. In certain preferred embodiments, the particles can actually be in a semi-solid form as long as the particles do not dissolve in the liquid or oil medium in which they are suspended before administration to the eye.

Preferred methods for forming semi-solid particles include hydrating substances such as gelatin, collagen or polymers immediately before insertion or placing soft hydrated solids in a mixture or ointment base that will not permit them to dehydrate.

Hydration is generally performed by exposure of the particles to an aqueous solution such that water is incorporated into the particles. The particles should remain hydrated when administered to the patient.

The bioerodible material particles can be hydrated by placing the material in the aqueous solution carrier discussed above. The aqueous carriers will hydrate the particles, and if the particles are left in the carrier, dehydration will be prevented.

Also, the bioerodible material can be hydrated by placing it in a drug soaking solution. Dehydration is prevented by placing the drug soaked particles in the aqueous carrier or in an ointment carrier. When dispersed in the ointment, the water will be retained in the particles and dehydration will thus be prevented by the ointment carrier.

When lipid is used as the bioerodible particle material, hydration is not necessary as lipid is already in a soft, malleable form.

Other methods for making materials which can be used for the particles of the invention malleable in form are known.

Although plasticizers are not the most preferred means to provide soft, malleable particles, examples of plasticizers which can be used in the present invention are shown in U.S. Pat. No. 4,179,497 to Cohen et al which shows large bioerodible inserts. A requirement of any plasticizers used is that the material be completely soluable in the ocular environment. Examples of suitable plasticizers include water, polyethylene glycol, propylene glycol, glycerine, trimethylol, propane, di and tripropylene glycol, hydroxypropyl sucrose and the like. Plasticizers can be present in the particles in various ranges. Although not the most preferred method of providing softness and malleability when plasticizers are used, they should be used in the lowest concentration possible and not greater than 20%.

Cohen et al recites a method of plasticizing a solid insert product with water. As applied to the present invention, the particles are contacted with air, having a relative humidity of at least about 40% until the particles pick up at least about 5% water, thereby becoming softer and more pliable. In certain preferred embodiments, the relevant humidity of the air is from about 60% to about 99% and the contact is continued until the water is present in the particles in amounts of from about 10% to about 20%.

Any bioerodible material which is compatible with any drug dispersed therein, is non-toxic, has the desired encapsulation properties or properties for dispersion of drug throughout, and has appropriate diffusion and erosion properties might also be used. The materials discussed above are examples of preferred embodiments, but should in no way limit the materials used for the particles of the present suspension.

There are several processes which can be used to form the bioerodible particles of the present invention.

One method includes using a liquid or a mixture of the bioerodible material which is poured onto a flat surface. The film created is then allowed to dry as the solvent evaporates. Once the film has dried, the individual particles can be cut using known methods. A variety of methods can be used to cut the film into individual particles. According to most embodiments, this cutting can be done by a preformed mold cutter having the proper dimensions.

These dimensions of the particles can be controlled during the particle forming process. For example, the thickness can be controlled by preparing the proper fluid phase of the bioerodible material. As an example, a solution of gelatin, collagen or carboxy methyl cellulose, for example, can be dried and then cut to the specific shape and dimensions or allowed to dry in appropriate molds.

According to certain preferred embodiments, the liquid mixture of bioerodible material is poured into a shallow pan or half-mold to the desired thickness. In certain embodiments, the pan or mold can include markings around the sides to indicate the thickness poured. In this way, the proper thickness can be assured. Subsequent to drying the particles are then cut in the remaining two dimensions.

In certain embodiments the liquid phase of the bioerodible material is not hydrated (the solvent is not aqueous). Further, even if the liquid phase is hydrated during pouring, the film or mold-forms are subsequently dehydrated when dried. In certain embodiments, the film or cut particles should be subsequently hydrated by soaking in an aqueous solution. The hydrated film or particles will expand to a certain degree depending on the amount of water incorporated therein. Thus, when determining the thickness of the film of bioerodible material which is not hydrated, the expected increase of thickness due to hydration should be compensated for by pouring a thinner film.

According to a separate application of the present invention, the specific dimensions of the bioerodible particles are chosen such that certain optimum treatment conditions are met. A system which provides these specific dimensions is the subject matter of a patent application filed on same date. In this unique system, the particles are formed with a greatest dimension of at least 0.5 mm, and a smallest dimension of no more than about 0.4 mm to 0.7 mm when disposed in the ocular environment.

Due to the specific minimum size of the largest particle dimension, the present invention provides optimum prevention of drainage through the punctum, and thus provides optimum prolonged delivery, as well as a predictable dosage that will remain in the eye. It should be noted that this specification is merely a minimum, and it is contemplated that the largest dimension be 4 mm or even greater to maximize the amount of material delivered. At the same time, due to the specific size of the smallest particle dimension in the ocular environment, the treatment system will not be uncomfortable or irritate the eye.

Further, if the particles are soft and malleable, such as when they are hydrated, the smallest dimension prior to administration to the eye can be increased above the preferred range. The soft material will be less irritating to the eye. Further, if placed between the eyelid and the eye, the particles will be compressed to the proper non-irritable range by the pressure between the eyelid and the eye. Also, as the particles are soft, they should conform to the eye and be comfortable even when disposed between the upper and lower eyelids. Thus, the thickness of the poured film can be increased when the particles are to be softened and thus malleable.

In certain preferred embodiments, the preferred hydrated thickness (smallest dimension) is in the range of about 0.5–0.75 mm. However, if malleable, especially if semi-solid in form, the smallest dimension can be up to 1 mm if administered to the eye between the eyelid and the eye where pressure will compress the particles to the proper thickness.

Pouring of the film is but one method of controlling the thickness. Other methods include pouring into molds of the proper dimension, and cutting dried masses of the material to the proper thickness. The method of forming the particular thickness should not be limited to the examples given above. Regardless of the method for forming the proper dimensions, the preferred ranges for this unique application of the present invention's unique dimensions are discussed below. Further, although these dimensions are preferred for certain applications, the present invention should in no way be limited to these dimensions.

In these embodiments, the smallest dimension of the three-dimensional particles should have a thickness of no greater than about 0.4 mm to 0.7 mm when placed in the ocular environment. Depending upon the composition of the particles, if compression of the particles is not expected in the ocular environment, the particles should be either cut to this specific smallest dimension, or have a film thickness of this dimension. However, in preferred embodiments, the bioerodible particles are made such that they are malleable, and thus can be cut to a size larger than the given range of the smallest dimension, as long as the particles will be deformed and compressed to the proper size range by the pressure between the eyelid and the eye. These methods of making the particles malleable are discussed above. Although the exact dimensions vary according to the specific materials and degree of deformation associated therewith, according to certain preferred embodiments, the particles that will be compressed should be cut such that the smallest dimension is no greater than 0.4 to 1.0 mm prior to administration to the eye, and should be compressed to the range of no more than 0.4 to 0.7 mm in the ocular environment.

The largest dimension of the particles should be at least 0.5 mm. The drainage system of the eye includes the punctum which is an opening or aperture on the radial aspect of both upper and lower eye lid margins (in the medial corner of the upper and lower eyelids).

The punctum has an average diameter of 0.5 mm. The punctum provides an opening into the drainage ducts or the lacrimal canaliculi of the drainage system which provides drainage of material out of the eye area. Material leaves the canaliculi, and passes through the lacrimal sac and nasolacrimal duct. Thus, the largest dimension of the particles should be greater than the size of the punctum to hinder drainage of the particles out of the eye through the punctum. It should be noted that 0.5 mm is merely a minimum value of the greatest dimension, and according to certain preferred embodiments, the largest dimension is generally 1 to 2 mm, but can be 4 mm or even greater to maximize the amount of material delivered. In certain preferred embodiments the third dimension or width should be about 0.5 mm or greater which further prevents drainage of the particles through the punctum.

The balance of the two dimensions as discussed above provides a system which will not drain from the eye area, and which will at the same time reduce the chance of injury or irritation to the eye even though the system includes particles large enough such that drainage through the punctum is prevented. Thus, prolonged, continuous treatment is provided without irritation of the eye and without need for meticulous application requiring special insertion devices.

However, as discussed above, the present invention should in no way be limited to these specific dimensional confines. It is contemplated that smaller particles be included in the present drug suspension, and it is also contemplated that larger particles be included in the present suspension. The only size requirement is that the particles can be suspended in a liquid or ointment carrier and subsequently administered to the eye in the suspension.

The particles can have any shape, including but not limited to: spheres, hemispheres, flat discs of any polygonal configuration, rounded discs, egg-shaped particles, cylinders, rods, elongated spaghetti-like forms, elongated box-forms, elongated ribbon forms and others.

As discussed above, in certain preferred embodiments, drug is dispersed throughout the particles prior to suspension in the carrier. This dispersion of the drug can include placing the drug component in the fluid form of the bioerodible material prior to forming the film, mixing the drug throughout and then pouring the film which is eventually cut into particles. According to other advantageous embodiments, the drug is added to the particles after cutting from the film. In these embodiments, the cut bioerodible particles are soaked in drug solution, and thereby absorb the drug. After the drug has been included in the bioerodible particles, the particles can then be suspended in the liquid medium.

It is contemplated that the amount of drug in the particles can be varied by soaking the particles in different concentrations of the drug. Further, different types of bioerodible material will absorb drug to varying extents. Thus, the amount of drug can be varied by using different types of bioerodible materials. Further, by varying the density of the particles, drug will be absorbed to different extents. For example, by increasing the particle material density, drug will be absorbed to a lesser degree than with a material less dense.

FIG. 1, shows a form of the particles 10 having bioerodible material 12 and drug 14 dispersed throughout according to certain preferred embodiments of the invention.

The drug can also be encapsulated inside an outer coating of the bioerodible material Encapsulation can be achieved by casting. The drug can be added to the bioerodible material while it is in liquid or particle form and the mixture can be reduced to fine microcapsules by grinding or other methods. Alternatively, fine particles of the drug can be coated such as by suspending dry particles of the drug in an air stream and contacting that stream with a stream of bioerodible material that coats the material with a wall of bioerodible material.

Another suitable microencapsulation method is the co-ascervation technique. The co-ascervation technique includes formation of three immiscible phases, a liquid manufacturing phase, a core material phase and a liquid coating phase. Liquid coating is deposited on the core material and rigidized usually by thermal, cross-linking or desolvation.

Encapsulated particles 20 are shown in FIG. 2, with a coating 12 of bioerodible material surrounding drug 14 according to certain preferred embodiments.

Once the particles are formed, they are then suspended in the liquid or ointment medium 16 (shown in FIGS. 1 and 2). The treatment system can include different types of particles having different drugs dispersed throughout. Further, the treatment system can include different types of bioerodible material in the particles such that a differentiated rate of erosion can be achieved, thus providing a time release system for continuous long-term release of material to the eye.

Although clearly not limited to the following range, approximately 5 to 10 particles should be included in each dose. However, this dose can change depending upon the size of the particles, the concentration of the drug, the type of drug, the treatment required for the specific patient, or for the specific condition. The particles in suspension can be included in a conventional eye dropper bottle which provides for simple self-administration. According to certain preferred embodiments, the particles are included in a single dose container. Thus, the entire dosage is included in a single container with a dispensing end which the patient opens and then drops the suspension into the eye. Thus, proper dosage is assured. As discussed above, the density of the liquid medium or the viscosity of the liquid medium can be used to assure uniform dispersion of the particles in the liquid medium or uniform dispersion can be provided by shaking immediately preceding administration.

According to the present invention, the liquid or ointment medium includes drug therein. Thus, the particles can include drug dispersed therein, as well as drug dispersed throughout the solution. Medication is immediately delivered to the eye in the solution and a prolonged dosage is provided by the bioerodible particles. If an immediate high concentration of drug is needed, a high concentration of drug in the solution can be provided. Further, it is contemplated to use particles having a drug dispersed therein different than the drug included in the solution. Thus, for different situations, drugs which are advantageously provided in a solution in a high dosage and which are not necessarily required over a period of time can be included in the solution and prolonged dosage of another drug can be provided in the particles.

In certain preferred embodiments, particles are dispersed in a standard eye ointment vehicle. The ointment can then be administered to the eye using standard procedures, For example, the lower eyelid is lifted out while the patient is looking up, and the ointment is then applied in the conjunctival sac. The lids should be closed for about one minute to allow the ointment to melt.

According to other advantageous features, a specific bioerodible material could be used which absorbs drug in relation to the concentration of the drug in which it is suspended. Thus, a single type of bioerodible material particle could be put into different concentrations of drug and thus provide different dosages of drug depending on the concentration in which it was suspended. Such a bioerodible material is placed in a solution including drug, and equalibrium between the particles and the solution would determine the exact concentration and duration of action.

The following examples are offered by way of illustration only and should not be construed as limiting the scope of the present invention in any way.

EXAMPLE I

A. A suspension of cross-linked collagen particles is prepared as follows:

Nine grams of collagen are added slowly with stirring to 40 grams of buffer solution at 90° C. The buffer solution includes one liter of distilled water, 7.1 grams of disodium hydrogen phosphate and 6.9 grams of sodium dihydrogen phosphate monohydrate. The PH should be 6.8. Forty Ml of the phosphate buffer and 0.15 grams chlorobutanol are combined with the heating and stirring. Alternatively, the collagen can be added to the buffer solution after it is cooled to room temperature and the mixture is then heated to 90° C. until the solution is complete.

The mixture is stirred thoroughly for four minutes until the temperature falls to 40° C. and is then poured onto a sheet of polyvinylchloride to a thickness which will give a dry thickness in the range generally of about 0.4 mm to 0.7 mm. The resulting film is dried at room temperature for one day.

A solution of formaldehyde (1% by weight) is prepared by addition of 13.1 grams of 38 percent formaldehyde reagent to 487 grams phosphate buffer (PH 6.8). The collagen films are submerged in this buffered formaldehyde solution for 20 minutes at room temperature, quickly rinsed with water and soaked in ice water for 2 hours. The films are removed from the ice water and dried overnight.

The dried film is then cut into individual particles using a mold cutter. The mold cutter forms disc-shaped particles having a diameter of 1.0 mm, and a thickness of 0.4 mm which was the thickness of the dried film.

B. The particles are then placed in a solution of tobramycin at 25° C. for 15 minutes. Concentration of drug in the solution is 40 mg per ml. The particles will absorb the drug solution.

The particles are then removed from the solution and allowed to dry for 2 hours.

A liquid medium made of sterile distilled water, 1%w. poly (vinyl alcohol), 0.004% benzalkonium chloride and 0.1% tobramycin is prepared.

A suspension of about 5 particles per 0.25 cc carrier medium is prepared. The drops of the suspension can be administered from a dispenser 30 by dropping the suspension into the eye. Specifically, in certain embodiments, the lower eyelid 32 is pulled down and the suspension 34 is dropped into the area 36 between the eyelid 32 and the eye 38 as shown in FIG. 3. One administration containing from about 3 to 6 particles will provide continuous delivery of tobramycin for about 6 hours.

EXAMPLE II

The particles for the suspension are prepared as described in Example IA. The particles are then suspended in a liquid medium made of sterile distilled water, 1%w poly (vinyl alcohol), 0.004% benzalkonium chloride and 0.1% dexamethasone. The suspension should be about 5 particles per 0.25 cc. The particles should be suspended for at least 20 minutes prior to administration.

The suspension described above is administered to the patient as described in Example IB.

EXAMPLE III

The particles for an ointment suspension are prepared as described in Example IA. The particles are then placed in a solution of garamycin at 25° C. for 20 minutes. Concentration of drug in the solution is 40 mg per milliliter. The particles will absorb the drug solution.

The particles including garamycin are then suspended in an ointment of petrolatum including 0.1% garamycin (40% solid petrolatum, 60% liquid petrolatum).

The ointment described above is administered to the patient using a tube with a wide dispenser opening.

EXAMPLE IV

The treatment suspension is prepared as described in Example IA except rather than pouring the liquid bioerodible mixture on a sheet of polyvinyl chloride, the mixture is poured into a mold. The mold forms particles in the shape of hemispheres (half spheres) having a thickness of about 0.4 mm and a diameter of about 1.0 mm.

EXAMPLE V

A. Nine grams of collagen are added slowly with stirring to 40 grams of buffer solution at 90° C. The buffer solution includes one liter of distilled water, 7.1 grams of disodium hydrogen phosphate and 6.9 grams of sodium dihydrogen phosphate monohydrate. The pH should be 6.8. Forty Ml of the phosphate buffer and 0.15 grams chlorobutanol are combined with the heating and stirring. Alternatively, the collagen can be added to the buffer solution after it is cooled to room temperature and the mixture is then heated to 90° C. until the solution is complete.

Three grams of cyclosporin are suspended in 5 ml of phosphate buffer. The resultant mixture is added immediately to the stirred collagen solution as it cools to approximately 50° C. The mixture is stirred thoroughly for four minutes until the temperature falls to 40° C. and is then poured onto a sheet of polyvinylchloride to a thickness which will dry to a thickness in the range of about 0.4 mm to 0.7 mm. The resulting film is dried at room temperature for one day.

A solution of formaldehyde (1% by weight) is prepared by addition of 13.1 grams of 38 percent formaldehyde reagent to 487 grams phosphate buffer (pH 6.8). The collagen films are submerged in this buffered formaldehyde solution for 20 minutes at room temperature, quickly rinsed with water and soaked in ice water for 2 hours. The films are removed from the ice water and dried overnight.

The dried film is then cut into individual particles using a mold cutter. The mold cutter forms disc-shaped particles having a diameter of 1 mm, and a thickness of 0.4 mm which was the thickness of the dried film.

B. The particles are then suspended in a liquid medium made of sterile distilled water, 1% w. poly(vinyl alcohol), 0.1% cyclosporin and 0.004% benzalkonium chloride. A suspension of about 5 particles per 0.25 cc of carrier medium is prepared.

The suspension is then administered as described in Example IB.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Method of treating the eye, comprising:
applying directly to the eye a suspension of at least one particle of bioerodable material including an opthalmic drug in one of a liquid carrier and an ointment carrier containing at least the same opthalmic drug as in said at least one particle of bioerodable material in the same chemical form and having a pH acceptable to the eye.

2. A method as in claim 1, wherein said at least one particle additionally includes a different drug than said drug in said carrier.

3. A method as in claim 1, wherein said carrier additionally includes a different drug than said drug disposed in said at least one particle.

4. A method as in claim 1, including a plurality of said particles, at least a portion of said particles including drug in a different concentration than at least another portion of said particles.

5. A method as in claim 1, including a plurality of said particles, at least a portion of said particles including a different drug than at least another portion of said particles.

6. A method as in claim 1, wherein a specific equilibrium between drug in said at least one particle and drug in said carrier provides a specific amount of drug to be delivered over a specific duration when administered to the ocular area.

7. A method as in claim 1, wherein said bioerodable material is at least one member selected from the group consisting of collagen, gelatin, polyvinyl alcohol, polymerized methycellulose and methyl cellulose derivatives.

8. A method as in claim 1, wherein said opthalmic drug is at least one member selected from the group consisting of idoxuridine, phenylephrine, pilocarpine and its acceptable salts, eserin, carachol, phospholine iodine, demecarium bromide, cyclopentolate, homatropine, scopolamine and epinephrine.

9. A method as in claim 1, wherein said opthalmic drug is at least one opthalmic steroid selected from the group consisting of hydrocortisone, hydrocortisone acetate, dexamethasone, dexamethasone 21-phosphate, fluocinolone, medrysone, prednisolone acetate, fluorometholone, betamethasone and triamcinoline.

10. A method as in claim 1, wherein said opthalmic drug is at least one antibiotic selected from the group consisting of tetracycline, chlorotetracycline, bacitracin, neomycin, polymyxin, granicidin, oxytetracycline, chloramphenicol, gentamycin, penicillin, erythromycin, tobry mycin, ciprofloxacin and norfloxacin.

* * * * *